United States Patent
Yoshikawa

(10) Patent No.: US 9,072,493 B1
(45) Date of Patent: Jul. 7, 2015

(54) ULTRASONIC DIAGNOSTIC APPARATUS AND ELASTIC EVALUATION METHOD

(71) Applicant: Hitachi Aloka Medical, Ltd., Mitaka-shi, Tokyo (JP)

(72) Inventor: Hideki Yoshikawa, Tokyo (JP)

(73) Assignee: Hitachi Aloka Medical, Ltd., Tokyo (JP)

( * ) Notice: Subject to any disclaimer, the term of this patent is extended or adjusted under 35 U.S.C. 154(b) by 0 days.

(21) Appl. No.: 14/635,159

(22) Filed: Mar. 2, 2015

Related U.S. Application Data

(63) Continuation of application No. 14/533,198, filed on Nov. 5, 2014.

(30) Foreign Application Priority Data

Nov. 8, 2013 (JP) .................................. 2013-232540

(51) Int. Cl.
 *A61B 8/00* (2006.01)
 *A61B 8/08* (2006.01)

(52) U.S. Cl.
 CPC .............. *A61B 8/485* (2013.01); *A61B 8/5223* (2013.01); *A61B 8/469* (2013.01); *A61B 8/463* (2013.01); *A61B 8/4444* (2013.01); *A61B 8/488* (2013.01); *A61B 8/5207* (2013.01)

(58) Field of Classification Search
 CPC ...... A61B 8/485; A61B 8/5223; A61B 8/469; A61B 8/463; A61B 8/4444; A61B 8/488; A61B 8/5207
 USPC ................................................. 600/437–469
 See application file for complete search history.

(56) References Cited

U.S. PATENT DOCUMENTS

| | | | |
|---|---|---|---|
| 8,118,744 B2 | 2/2012 | Palmeri et al. | |
| 2004/0260180 A1* | 12/2004 | Kanai et al. | 600/449 |
| 2007/0230763 A1 | 10/2007 | Matsumoto et al. | |
| 2009/0163805 A1* | 6/2009 | Sunagawa et al. | 600/438 |

(Continued)

FOREIGN PATENT DOCUMENTS

| | | |
|---|---|---|
| JP | 11-221219 A | 8/1999 |
| WO | 2012077579 A1 | 6/2012 |

OTHER PUBLICATIONS

Liexiang Fan, et al "Classifying Ultrasound Image Regions by Using Characteristics of the ARFI Induced Tissue Displacement Temporal Profile", 2011 IEEE International Ultrosonics Symposium Proceedings, vol. 2, p. 1364-1367.

*Primary Examiner* — Sanjay Cattungal
(74) *Attorney, Agent, or Firm* — Brundidge & Stanger, P.C.

(57) ABSTRACT

An ultrasonic diagnostic apparatus and a method having a highly-reliable elastic evaluation unit for tissues. The invention includes a signal processing unit that processes received data obtained after ultrasonic waves are transmitted and received to/from an inspection target through a probe. An ROI detection unit of the processing unit obtains a distance index indicating a region proper for an elastic evaluation based on brightness distribution of the received data obtained by transmitting and receiving first ultrasonic waves to/from the probe, and sets an ROI based on the distance index. Then, second ultrasonic waves are transmitted to the ROI to generate shear waves. An elastic evaluation unit calculates a shear wave velocity based on received data obtained by transmitting and receiving third ultrasonic waves in the ROI, and outputs the shear wave velocity and an elastic evaluation value of the ROI as a reliability index.

14 Claims, 13 Drawing Sheets

(56) References Cited

U.S. PATENT DOCUMENTS

| | | |
|---|---|---|
| 2009/0216119 A1 | 8/2009 | Fan et al. |
| 2010/0016718 A1 | 1/2010 | Fan et al. |
| 2010/0222678 A1 | 9/2010 | Bercoff et al. |
| 2011/0026800 A1 | 2/2011 | Tonomura et al. |
| 2011/0028838 A1 | 2/2011 | Pernot et al. |
| 2012/0136250 A1* | 5/2012 | Tabaru et al. ............. 600/438 |
| 2012/0158323 A1* | 6/2012 | Hazard et al. ............. 702/56 |
| 2012/0271166 A1* | 10/2012 | Shao et al. ............. 600/438 |
| 2012/0310089 A1 | 12/2012 | Miyachi et al. |
| 2013/0102932 A1* | 4/2013 | Cain et al. ............. 601/2 |
| 2013/0165789 A1 | 6/2013 | Yao et al. |
| 2013/0289402 A1 | 10/2013 | Tabaru et al. |

* cited by examiner

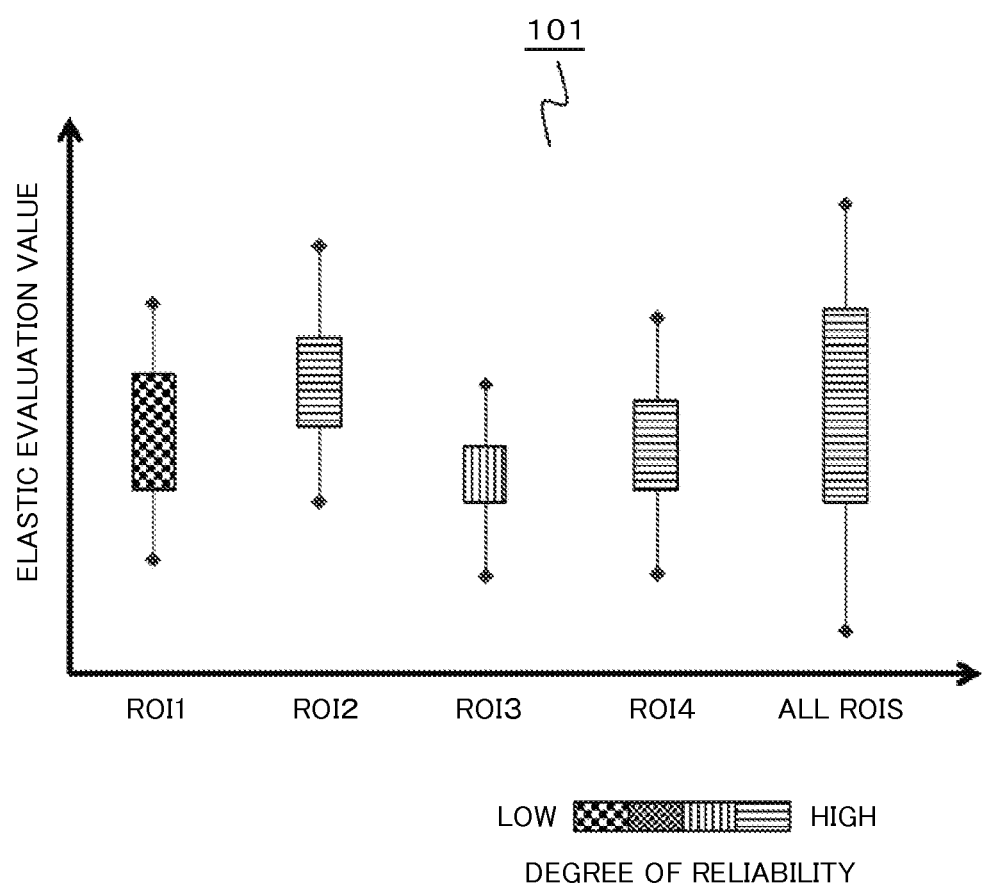

FIG. 11

EQUATION 1  $\bar{I} = \dfrac{1}{N}\sum_{n=1}^{N} I_n$     $N$: NUMBER OF PIXELS OF ROI
$I_n$: BRIGHTNESS OF CONFIGURATION PIXELS EQUATION 2  $\bar{I}_s = \dfrac{1}{1+\exp(-a\cdot(\bar{I}+b))}$ EQUATION 3  $\sigma = \sqrt{\dfrac{1}{N}\sum_{n=1}^{N}(I_n - \bar{I})^2}$ EQUATION 4  $\sigma = \dfrac{\sigma - \sigma_{min}}{\sigma_{max} - \sigma_{min}}$    $\sigma_{min}$: MINIMUM VALUE OF $\sigma$ IN ENTIRE IMAGE
$\sigma_{max}$: MAXIMUM VALUE OF $\sigma$ IN ENTIRE IMAGE EQUATION 5  $d = \sqrt{\sigma^2 + (1-\bar{I}_s)^2}$ FIG. 13
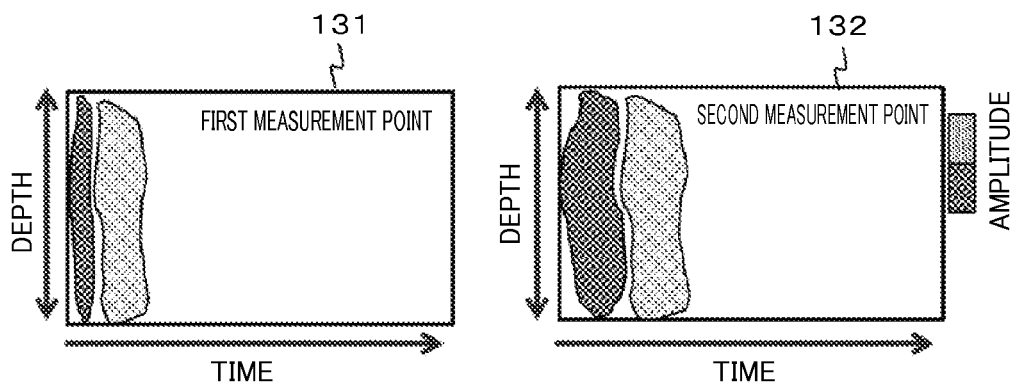
CALCULATE PTtr1 AND PTtr2 ON THE BASIS OF MINIMUM VALUES REPRESENTED BY BLACK SPOTS
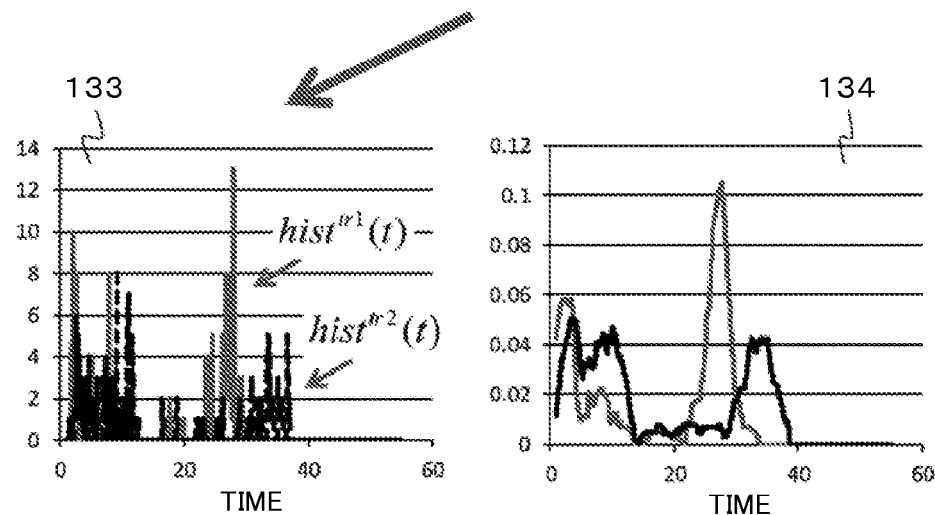
CALCULATE HISTOGRAM ⟹ APPLY SMOOTHING FILTER EQUATION 6 $\quad R = \dfrac{\sum\limits_{t=1}^{T} hist^{r1}(t) \cdot hist^{r2}(t)}{\sqrt{\sum\limits_{t=1}^{T} hist^{r1}(t)^2 \times \sum\limits_{t=1}^{T} hist^{r2}(t)^2}}$

ULTRASONIC DIAGNOSTIC APPARATUS AND ELASTIC EVALUATION METHOD

CROSS REFERENCE TO RELATED APPLICATIONS

The present application is a Continuation Application of application Ser. No. 14/533,198, filed Nov. 5, 2014; which claims priority from Japanese patent application JP2013-232540, filed on Nov. 8, 2013, the contents of which are hereby incorporated by reference into this application.

BACKGROUND OF THE INVENTION

The present invention relates to an ultrasonic diagnostic apparatus, and particularly to a technique of generating shear waves in a living body using acoustic radiation force to evaluate the elasticity using the propagation velocity.

Medical image display apparatuses typified by ultrasonic waves, MRI (Magnetic Resonance Imaging), and X-ray CT (Computed Tomography) have been widely used as apparatuses that present information in a living body that cannot be visually confirmed in the form of values or images. Among those, an image display apparatus using ultrasonic waves is provided with a high degree of temporal resolution as compared to the other apparatuses, and has performance capable of imaging a pulsating heart without blurring.

Ultrasonic waves propagating in a living body are mainly classified into longitudinal waves and transverse waves, and information of the longitudinal waves (a sound velocity of about 1540 m/s) is mainly used in many techniques used in products, namely, techniques of visualizing tissue configurations and measuring a blood velocity.

Recently, a technique of evaluating the elastic modulus of a tissue using transverse waves (hereinafter, referred to as shear waves) attracts attention, and is being used for mammary tumors and chronic liver disease in clinical practice. In the technique, shear waves are allowed to be generated inside a tissue as a measurement target, and the elasticity is evaluated on the basis of the propagation velocity. The techniques of generating the shear waves are roughly classified into a mechanical method and a radiation pressure method. The mechanical method is a method in which a vibration of about 1 kHz is applied to a body surface using a vibrator or the like to generate the shear waves, and a driving apparatus serving as a vibrating source is necessary. On the other hand, in the radiation pressure method, acoustic radiation pressure is applied to the inside of a living body using focused ultrasonic waves that allow ultrasonic waves to be locally concentrated in a tissue, and the shear waves are allowed to be generated using following tissue displacement. Each method is a technique in which the tissue displacement caused by propagation of the generated shear waves is measured using ultrasonic waves to evaluate information related to hardness of the tissue.

As prior art documents related to these techniques, for example, U.S. Pat. No. 8,118,744B2 and US2010/0222678A1 relate to a method of an elastic evaluation using acoustic radiation pressure.

BRIEF SUMMARY OF THE INVENTION

In the method described in the above-described patent documents, radiation force is allowed to be generated in a tissue using focused ultrasonic waves to propagate shear waves in the tissue. Plural measurement points where ultrasonic waves are transmitted and received are provided in the propagation direction to measure time changes of tissue displacement. Using the measurement result of the displacement, a feature value (PT (Peak to time), zero-cross point, and so on), to show the spatial distribution of the shear waves at each measurement point is measured. As a typical approach to use the PT at each measurement point, the propagation time of the shear waves between the measurement points is calculated to measure the velocity.

In the case where tissue structures such as blood vessels and fibrous tissues exist on a propagation route of the shear waves, the wavefront is scattered due to affects of diffraction and refraction, and the shape of the wavefront is disordered. In a method of estimating the shear wave velocity using the amount of displacement of a tissue caused by propagation, the wavefront disorder is a major factor of increasing errors of the elastic evaluation. Further, there is no means to evaluate the reliability of the measurement result of the velocity measured under the circumstances, and thus the objectivity is disadvantageously low.

An object of the present invention is to provide an ultrasonic diagnostic apparatus and an elastic evaluation method having a highly-reliable elastic evaluation unit for tissues.

In order to achieve the above-described object, the present invention provides an ultrasonic diagnostic apparatus including: a transmission/reception unit that transmits and receives first, second, and third ultrasonic waves to/from an inspection target through a probe that transmits and receives ultrasonic waves; and a processing unit that processes received data obtained from the inspection target, wherein the processing unit can determine a measurement region on the basis of image information formed using the received data obtained by transmitting and receiving the first ultrasonic waves, can transmit the second ultrasonic waves to the determined measurement region to generate shear waves, can calculate a shear wave velocity using the received data obtained by transmitting and receiving the third ultrasonic waves to/from the measurement region, and can output the shear wave velocity and an elastic evaluation value of the measurement region.

Further, in order to achieve the above-described object, the present invention provides an elastic evaluation method in an ultrasonic diagnostic apparatus including the steps of: transmitting and receiving first ultrasonic waves to/from an inspection target through a probe that transmits and receives ultrasonic waves; generating brightness distribution of an inspection target on the basis of received data obtained from the inspection target; determining a measurement region on the basis of the generated brightness distribution; transmitting second ultrasonic waves to the determined measurement region to generate shear waves; calculating a shear wave velocity using the received data obtained by transmitting and receiving third ultrasonic waves to/from the measurement region; and outputting the shear wave velocity and an elastic evaluation value of the measurement region.

According to the present invention, an elastic evaluation can be performed at a region where velocity measurement with a high degree of accuracy can be expected, and the reliability of the result can be determined on the basis of objective elastic evaluation values. The highly-reliable elastic evaluation for tissues can be realized, so that shortening of inspection time of an ultrasonic diagnostic apparatus, lessening of a load placed on operators and patients, and improvement of the accuracy rate of diagnosis can be expected.

BRIEF DESCRIPTION OF THE DRAWINGS

FIG. 10 is a diagram for showing an example of a display configuration of values of elastic evaluation results according to the first embodiment;

FIG. 11 is a diagram for showing equations related to processing methods according to the first embodiment;

FIG. 13 is a diagram for explaining calculation of a histogram according to the second embodiment;

DETAILED DESCRIPTION OF THE INVENTION

Figure 1:
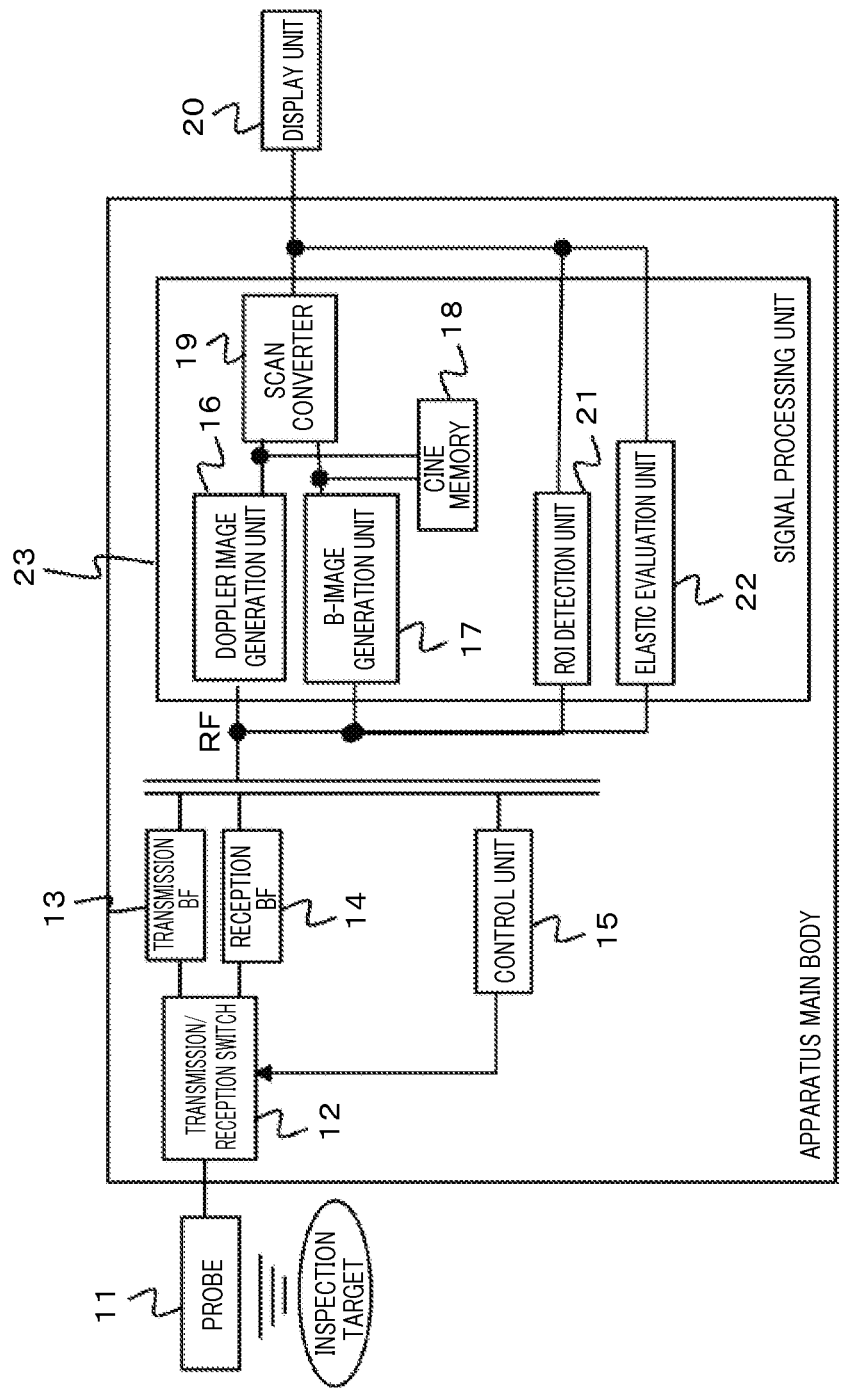
FIG. 1 is a block diagram for showing a configuration example of an ultrasonic diagnostic apparatus according to a first embodiment.

Hereinafter, embodiments of the present invention will be described in accordance with the drawings. It should be noted that information used for an elastic evaluation for tissues in the specification indicates general physical properties of tissues such as distortion, a shear wave velocity, a longitudinal wave velocity, a Young's modulus, the modulus of rigidity, the modulus of volume elasticity, a Poisson's ratio, and a viscosity coefficient. However, the present invention will be described using the shear wave velocity. Further, information used for the elastic evaluation in an ultrasonic diagnostic apparatus according to the present invention, for example, structural objects such as blood vessels, local fibrous tissues, and cysts of a living body that is an inspection target for which the shear wave velocity is measured are referred to as tissue structures or structural objects. Further, an elastic evaluation value in the specification means a reliability index of a result of the elastic evaluation in a measurement region, and is a value indicating the reliability of a result of the elastic evaluation in each measurement region.

First Embodiment

The first embodiment is an embodiment of an ultrasonic diagnostic apparatus and an elastic evaluation method. The ultrasonic diagnostic apparatus includes a transmission/reception unit that transmits and receives first, second, and third ultrasonic waves to/from an inspection target through a probe that transmits and receives ultrasonic waves and a processing unit that processes received data obtained from the inspection target. The processing unit can determine a measurement region on the basis of image information formed using the received data obtained by transmitting and receiving the first ultrasonic waves, can transmit the second ultrasonic waves to the determined measurement region to generate shear waves, can calculate a shear wave velocity using the received data obtained by transmitting and receiving the third ultrasonic waves to/from the measurement region, and can output the shear wave velocity and an elastic evaluation value of the measurement region.

Further, the embodiment is an embodiment of an ultrasonic diagnostic apparatus and an elastic evaluation method in which an index indicating a region proper for the elastic evaluation is calculated on the basis of brightness distribution of the inspection target calculated using the image information to determine the measurement region on the basis of the index.

A configuration example of an ultrasonic diagnostic apparatus and a measurement method of a shear wave velocity in the first embodiment will be described using a block diagram of FIG. 1. In the configuration of the ultrasonic diagnostic apparatus of the embodiment, the measurement region where the shear wave velocity is measured is referred to as an ROI (Region of Interest). A signal processing unit 23 includes, as will be described later, an ROI evaluation unit 21 that calculates an index indicating a region proper for the elastic evaluation on the basis of the brightness distribution of the image information to determine the measurement region on the basis of the image information formed using the received data and that detects the measurement region on the basis of the calculated index, and an elastic evaluation unit 22 that evaluates the elasticity of a tissue in the measurement region using the shear wave velocity and the like measured in the measurement region. The signal processing unit 23 is a general term of a module that processes signals on the basis of RF (Radio Frequency) data. In this case, the index indicating the region proper for the elastic evaluation is, as will be described later using equations, a distance index that is calculated on the basis of the brightness distribution of the image information generated using the received data and that objectively indicates a homogeneous region with less tissue structures and with a sufficient degree of brightness for measurement of shear waves.

First, a configuration related to generation of RF data and image data used in the embodiment will be described. An electric signal for a transmission pulse is transmitted, through a digital/analog (D/A) converter (not shown in the drawing), from a transmission beamformer (BF) 13 that generates ultrasonic signals to a probe 11 that is placed on a body surface of the inspection target described in FIG. 1 and that transmits and receives ultrasonic waves. The electric signal input to the probe 11 is converted to an acoustic signal by ceramic elements placed inside to be transmitted to the inside of the test body. The transmission is performed by plural ceramic elements, and predetermined time delays are set for the respective elements to be focused at a predetermined depth in the test body.

The acoustic signal reflected in the course of propagation in the inspection target is received by the probe 11 again, and is converted to an electric signal contrary to the transmission. Then, the electric signal is transmitted as received data to a reception beamformer (reception BF) 14 that generates complex RF data from the received ultrasonic signals through an analog/digital (A/D) converter (not shown in the drawing). Switching of transmission and reception is carried out by a transmission/reception switch SW 12 on the basis of control of a control unit 15 that is a processing unit. The reception BF 14 performs an adding process (phasing addition) for the signals received by the plural elements in consideration of the time delays set at the time of transmission. Then, after an attenuation correction process and the like are performed, the signals are transmitted, as the complex RF data, to a Doppler image generation unit 16 that generates a Doppler image indicating the velocity and direction of blood flow or to a B-image generation unit 17 that generates a brightness (B)-mode image (hereinafter, referred to as B-image) representing configuration information of tissues from the RF data in the signal processing unit 23 that is a processing unit. It should be noted that the probe 11, the transmission/reception switch SW 12, the transmission BF 13, and the reception BF 14 are collectively referred to as an ultrasonic wave transmission/reception unit in the specification.

The RF data input to the signal processing unit 23 from the reception BF 14 of the ultrasonic wave transmission/reception unit becomes element data in a specific line along the transmission/reception direction of ultrasonic waves among plural pieces of image data that are finally displayed on the display unit 20. The transmission and reception of the ultrasonic waves to/from the inspection target are sequentially switched to each other in the arrangement direction of the ceramic elements configuring the probe 11, so that the RF data can be obtained as all received data serving as configuration elements of image data.

For the RF data that is received data obtained from the ultrasonic wave transmission/reception unit, image generation processes such as gain control, logarithmic compression, and envelope detection that are generally used in a common ultrasonic diagnostic apparatus are performed by the B-image generation unit 17 of the signal processing unit 23, and the B-image representing configuration information in the inspection target is generated.

On the other hand, the Doppler image generation unit 16 of the signal processing unit 23 calculates the velocity and direction as blood flow information using a correlation operation to generate the Doppler image. It should be noted that the generation of the Doppler image is different from that of the B-image in transmission and reception sequences of the ultrasonic waves. However, the technical content thereof is generally known, and thus the detailed explanation thereof will be omitted. The B-image and the Doppler image are stored in a cine memory 18. Coordinate transformation and pixel interpolation are performed for the generated B-image and Doppler image by a scan converter 19 in accordance with the type of the probe to be displayed on the display unit 20 that displays these images, evaluated images, and values.

As shown in FIG. 1, the signal processing unit 23 further includes an ROI detection unit 21 that detects an ROI that is a measurement region with less tissue structures and a high degree of brightness and an elastic evaluation unit 22 that calculates a shear wave velocity on the basis of the received data in the ROI.

As will be described later in detail using the drawings, the ROI detection unit 21 of the signal processing unit 23 detects a tissue structure that affects scattering of shear waves using the RF data received from the reception BF 14, and further detects whether or not the tissue structure has a sufficient degree of brightness for measurement of the shear waves. Further, the ROI detection unit 21 calculates an index indicating a region proper for the elastic evaluation, in other words, a distance index to determine properness for measurement of the shear wave velocity using the tissue structure and brightness distribution that is information of brightness.

The ROI detection unit 21 of the signal processing unit 23 calculates the distance index on the basis of a generally-known index such as a statistical value of brightness in a certain range of the inspection target, for example, an average value, standard deviation, dispersion, entropy, an eigenvalue, a kurtosis, or the like. The distance index is calculated in all regions of candidates of the elastic evaluation, and an image for determination is generated in accordance with the value of the calculated distance index. Further, on the basis of the image for determination, the ROI that is the optimum measurement region for measurement of the shear wave velocity where lessening of wavefront disorder can be expected is automatically selected. The image for determination is preferably displayed as a color map having a color pattern as will be described later. Specifically, the color map used as the image for determination of the inspection target is displayed on the display unit 20 on the basis of the value of the distance index calculated by the signal processing unit 23.

Figure 2:
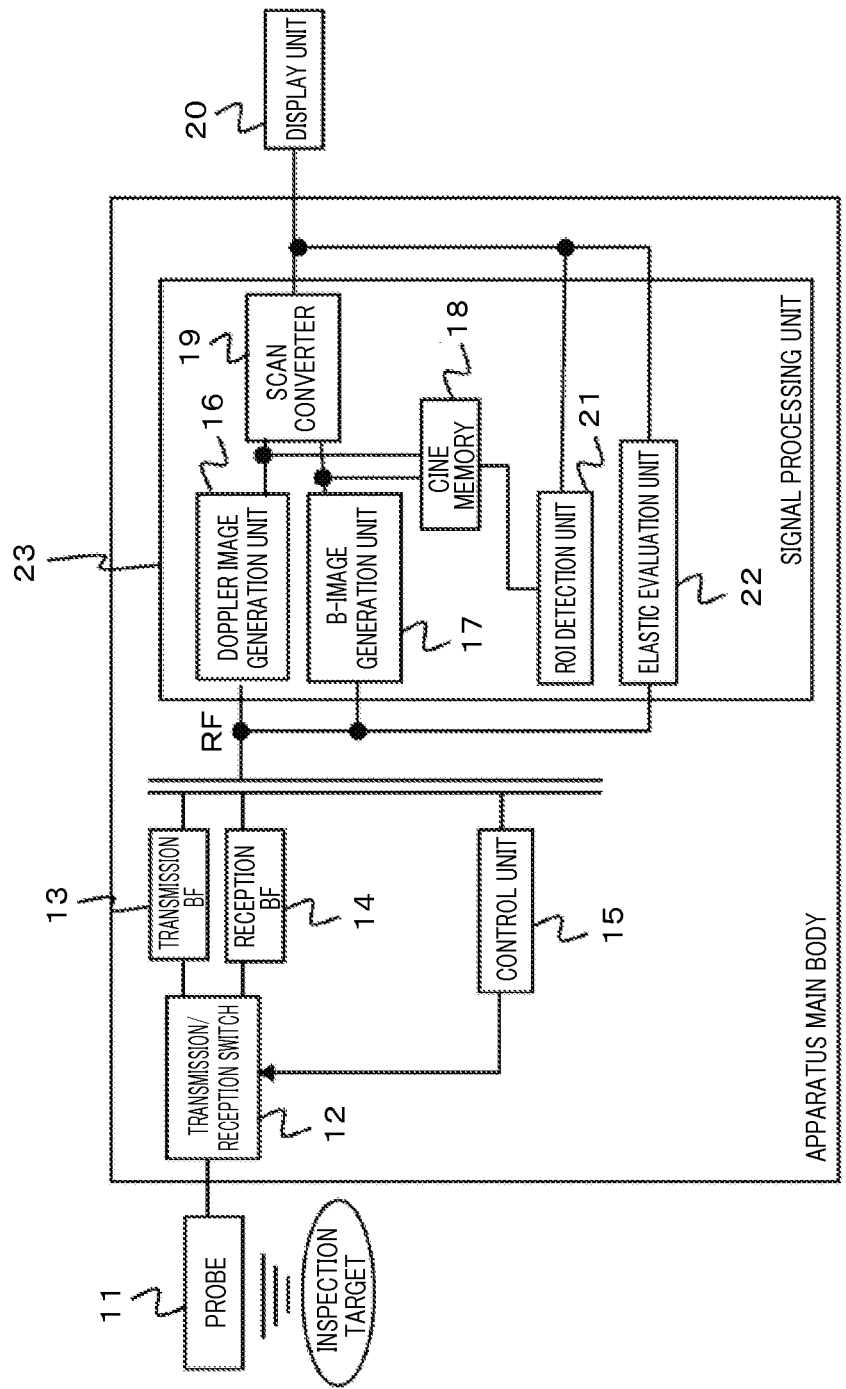
FIG. 2 is a block diagram for showing another configuration example of the ultrasonic diagnostic apparatus according to the first embodiment.

It should be noted that the ROI detection unit 21 generates the image for determination on the basis of the brightness information of the image using the RF data in the configuration of the ultrasonic diagnostic apparatus shown in FIG. 1. However, as shown in a modified configuration example of the ultrasonic diagnostic apparatus of FIG. 2, the image for determination can be similarly generated on the basis of the brightness information of the image using the image data stored in the cine memory 18. The configuration of the ultrasonic diagnostic apparatus of FIG. 2 is different from that of FIG. 1 only in the above-described point, and the other configurations are the same. The elastic evaluation unit 22 of the signal processing unit 23 transmits burst waves that are the second ultrasonic waves in the ROI determined by the ROI detection unit 21 and transmits and receives track pulses that are the third ultrasonic waves to evaluate information related to the elasticity of the tissue.

It should be noted that the control unit 15 and the signal processing unit 23 that control entire data flows and processes in the apparatus main body in the configuration of the ultrasonic diagnostic apparatus of the embodiment shown in FIGS. 1 and 2 can be realized using a general computer configuration having a CPU (Central Processing Unit) and a memory. Specifically, the units except the cine memory 18 and the scan converter 19 realized by hardware as needed can be realized by program processing by the CPU. Thus, the signal processing unit 23 together with the control unit 15 is referred to as a processing unit in the specification. It should be noted that when using a general computer, a display of the computer can be used as the display unit 20.

Next, a configuration of the elastic evaluation unit 22 of the signal processing unit 23 in the configuration of the embodiment shown in FIG. 1 and FIG. 2 will be described in detail using a block configuration diagram of FIG. 3. As described above, the respective functional units included in the elastic evaluation unit 22 can be realized by program processing by the CPU.

Figure 3:
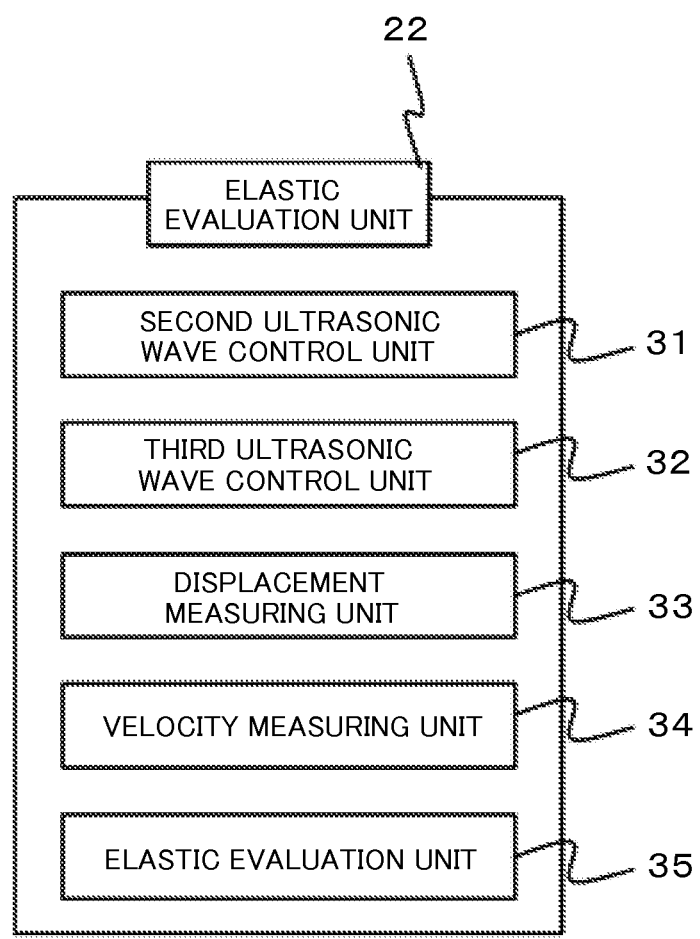
FIG. 3 is a diagram for showing a configuration of an elastic evaluation unit according to the first embodiment.

As shown in FIG. 3, the elastic evaluation unit 22 includes a second ultrasonic wave control unit 31, a third ultrasonic wave control unit 32, a displacement measuring unit 33, a velocity measuring unit 34, and an elastic evaluation unit 35. In this case, the second ultrasonic wave control unit 31 determines acoustic parameters necessary for wave transmission such as a focused position, a transmission angle, a burst length, voltage, a frequency, and the number of driving elements that are wave transmission conditions of the ultrasonic burst waves to generate a radiation pressure in the ROI that is a measurement region detected and determined by the ROI detection unit 21. Further, the third ultrasonic wave control unit 32 determines acoustic parameters necessary for wave transmission such as a focused position, a transmission angle, the number of waves, voltage, a frequency, the number of times of transmission and reception, and the number of driving elements that are wave transmission conditions of the track pulses that are ultrasonic pulse waves to measure the displacement of the tissue on the basis of coordinate information. The displacement measuring unit 33 measures the displacement of the tissue using the RF data output from the ultrasonic wave transmission/reception unit. The velocity measuring unit 34 measures the shear wave velocity using the result of the displacement measuring unit 33. The elastic evaluation unit 35 evaluates elastic information of the tissue using the result of the velocity measuring unit 34.

In this case, the elastic information for the elastic evaluation of tissues indicates general physical properties related to deformation and flowage of materials such as distortion, a shear wave velocity, a longitudinal wave velocity, a Young's modulus, the modulus of rigidity, the modulus of volume elasticity, a Poisson's ratio, and a viscosity coefficient. It should be noted that PT (Peak to time) of the shear waves can be calculated using the wavefront characteristic amount such as a maximum value, a minimum value, and an intermediate value between the maximum value and the minimum value on the basis of time changes of displacement measured by the displacement measuring unit 33.

In FIG. 3, the second ultrasonic wave control unit 31 first determines the wave transmission conditions of push pulses as the second ultrasonic waves on the basis of the position coordinate of the ROI that is the designated measurement region. As the wave transmission conditions under which a living body is less affected and the shear waves can be effectively generated, a focused condition in which the F number is about 1 to 2 (a value obtained by dividing the width of the aperture by the focal depth) is appropriate. In addition, as a strength and a burst length, a strength in a range of 0.1 to 1 kW/cm$^2$ and a burst length in a range of 100 to 1000 μs are appropriate.

In this case, the width of the aperture is a range of the ceramic elements that are actually driven, and a discrete value of the element interval is used. Apodization that sets an aperture weight is performed for voltage applied to each element to form an optimum focal range, and the weight is reduced from the center of the aperture towards the corners, so that the disorder of the focal range affected by diffraction is suppressed. However, the aperture weight disadvantageously reduces the strength. Thus, in the case where the evaluation position is deep and largely affected by attenuation, the aperture weight is lessened by giving priority to the strength over the formation of regions in some cases. Further, the transmission frequency is effective around the center frequency of the sensitivity bandwidth of the probe 11. The wave transmission conditions of the push pulses determined by the second ultrasonic wave control unit 31 are immediately transmitted to the transmission BF 13 through the control unit 15, and irradiation to the inside of the living body is performed from the probe 11.

Thereafter, the third ultrasonic wave control unit 32 determines the wave transmission conditions of the track pulses that are the third ultrasonic waves. The acoustic parameters such as a frequency, the number of waves, and an F number are almost the same as the conditions under which the image data is generated. If the inspection target is an abdomen, conditions in which the frequency is 1 to 5 MHz, the number of waves is 1 to 3, and the F number is 1 to 2 are used.

A reflected signal from the living body obtained by transmission of the track pulses is transmitted to the reception BF 14 through the probe 11, and complex RF data is generated. The RF data is input to the displacement measuring unit 33, and displacement of the tissue caused by propagation of the shear waves is measured. The displacement measuring unit 33 measures the displacement of the tissue using a complex correlation operation between the pieces of RF data obtained at time intervals of PRT (Pulse Repetition Time). The displacement measuring unit 33 of the embodiment calculates a particle velocity as displacement in a unit of time. There is a method in which the absolute value of displacement is calculated on the basis of the RF data before transmission of the push pulses. However, if the particle velocity is used, low frequency components caused by swing of the probe and natural movement of body tissues can be effectively removed to measure the shear waves at a high degree of sensitivity, as compared to the absolute value of displacement.

The above-described operation by the displacement measuring unit 33 is performed for all RF signals obtained by the ultrasonic wave transmission/reception unit, and the shear wave velocity is calculated by the velocity measuring unit 34 on the basis of the particle velocity that is the calculated displacement information.

Finally, the elastic information of the tissue, namely, the physical properties of the tissue such as distortion, a shear wave velocity, a longitudinal wave velocity, a Young's modulus, the modulus of rigidity, the modulus of volume elasticity, a Poisson's ratio, and a viscosity coefficient are evaluated by the elastic evaluation unit 35 on the basis of the measured shear wave velocity.

Next, the calculation of the distance index that is an index indicating a region proper for the elastic evaluation on the basis of the brightness distribution of the inspection target in the ROI detection unit 21 that detects an ROI that is a measurement region of the signal processing unit 23 in the apparatus of the embodiment and detailed content leading to the determination of the ROI on the basis of the distance index will be described on the basis of a flowchart of FIG. 4. As described above, the distance index is calculated on the basis of a generally-known index such as a statistical value of brightness distribution in a certain range, for example, an average value, standard deviation, dispersion, entropy, an eigenvalue, a kurtosis, or the like. The distance index is calculated to determine the ROI that is a region proper for the elastic evaluation by measurement of the shear waves on the basis of the brightness distribution. The determination conditions include no tissue structures causing the wavefront disorder and a sufficient signal strength for an operation of displacement measurement. Thus, the former is evaluated using the standard deviation of the brightness distribution, and the latter is evaluated using the average brightness of the brightness distribution in the configuration of the embodiment. As a value uniquely evaluating the both, the distance index is defined.

Figure 4:
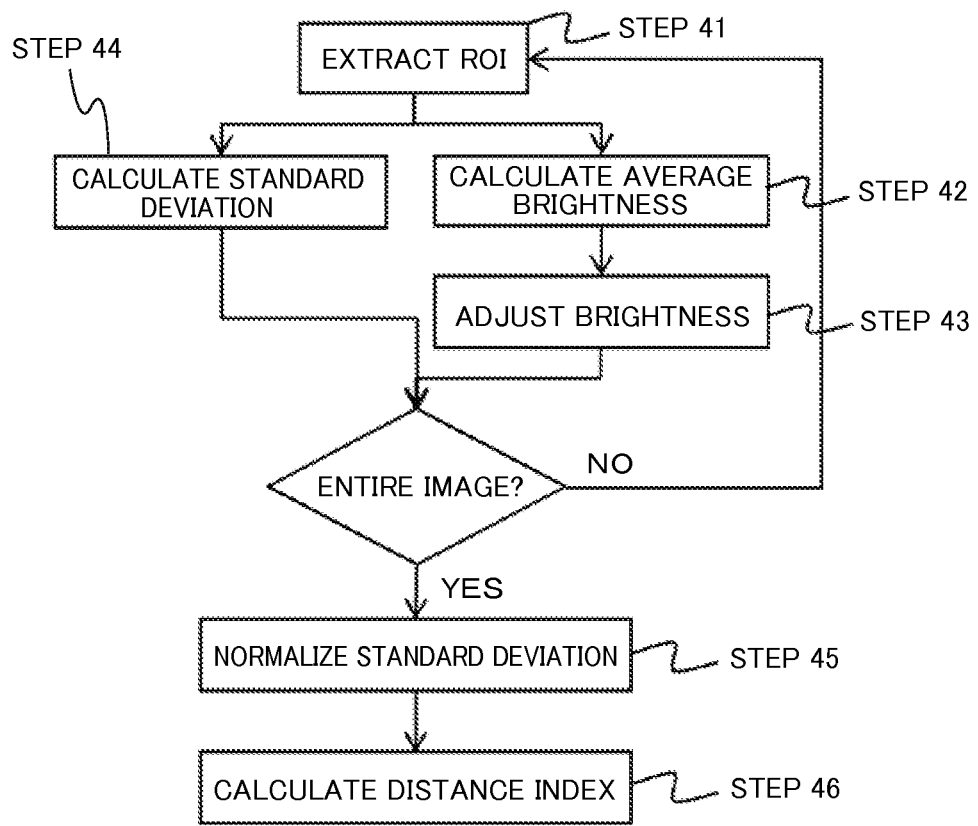
FIG. 4 is a diagram for showing a flowchart in an ROI detection unit according to the first embodiment.

As shown in FIG. 4, the ROI detection unit 21 first extracts an ROI as a candidate region where the shear waves are measured using data of the B-image obtained by transmitting and receiving the first ultrasonic waves that are pulse signals in Step 41.

In Step 42, the average brightness of the extracted ROI is calculated using Equation 1 shown in FIG. 11. Further, brightness adjustment for the calculated brightness is performed in Step 43. As the brightness adjustment, an S-shaped function is preferable. In other words, the average brightness that is the average value of brightness after performing the adjustment process by the S-shaped function is used as a representative statistical value. The average brightness serves as an index of measured sensitivity.

Figure 5:
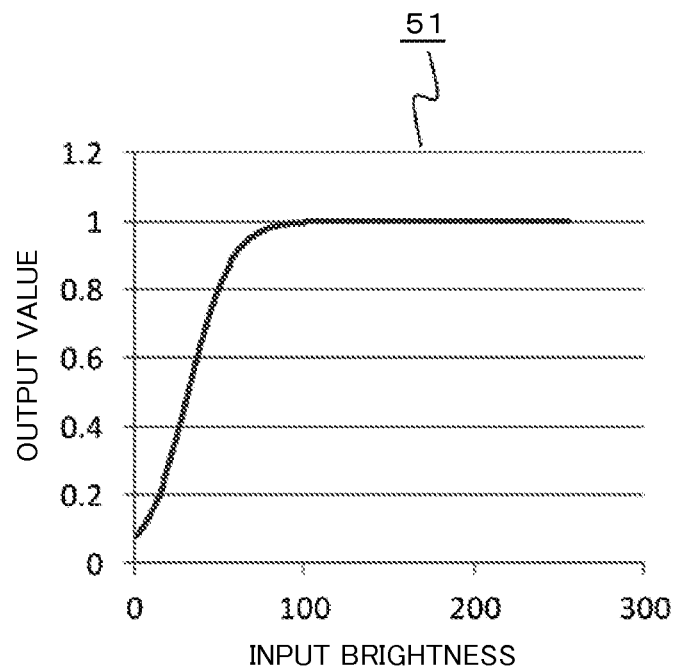
FIG. 5 is a diagram for showing an example of a function used for brightness adjustment according to the first embodiment.

FIG. 5 shows a graph 51 as an example of a function in the case where the brightness adjustment is performed for a 256-gradation image using a sigmoid function (Equation 2). In the drawing, the horizontal axis represents input brightness of 0 to 256 gradations, and the vertical axis represents output values. As being apparent from the shape of the sigmoid function in the drawing, the result of the brightness adjustment lessens the difference between the middle brightness and the high brightness, and further defines the discrimination from the low brightness. As described above, the input brightness is an index related to measurement of displacement. If the input brightness is sufficient for the measurement of displacement, the condition related to the brightness is satisfied. Thus, it is not necessary to discriminate the middle brightness from the high brightness. On the contrary, there is a possibility that a high-brightness region with uneven brightness distribution such as a superficial region or a region including a nodule is wrongly detected.

In Step 44, the standard deviation of the ROI that is the extracted candidate region is calculated (Equation 3). The standard deviation serves as an index of the wavefront disorder. The average brightness and the standard deviation are calculated in the entire image. It should be noted that the ROI extracted as a candidate region is extracted in all pixels on the image. In Step 45, the standard deviation is normalized (Equation 4). By performing the process, the standard deviation of the general population calculated in the entire image is adjusted in a range of 0 to 1.

Figure 6:
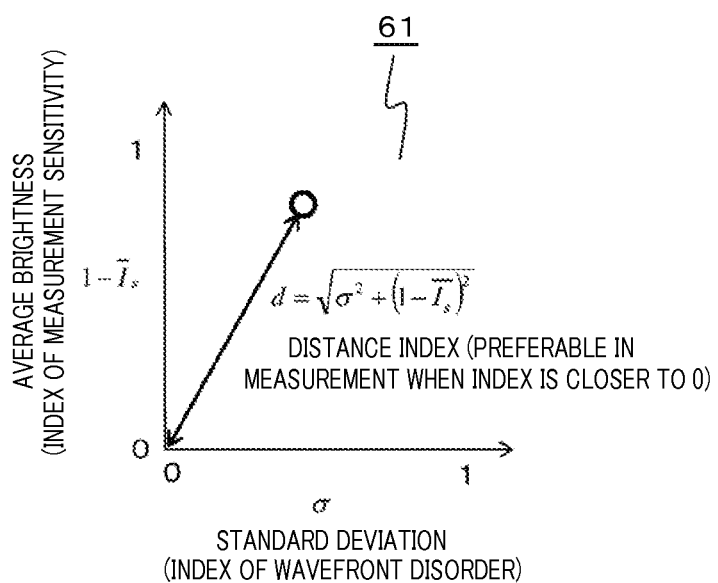
FIG. 6 is a diagram for showing an example of a distance index according to the first embodiment.

In Step 46, the distance index is calculated on the basis of the average brightness and the standard deviation in accordance with Equation 5. FIG. 6 schematically shows an example of the distance index as a graph 61. As shown in FIG. 6, an ROI with a smaller value of the distance index is determined as a high-brightness region having a homogeneous tissue structure. Specifically, the ROI is a region with less wavefront disorder where the measurement of displacement can be performed at a high degree of sensitivity and the measurement of the shear wave velocity at a high degree of reliability can be expected. As the value of the distance index is closer to 0, the region is preferable and proper for the elastic evaluation. As the value of the distance index is closer to 1, the region is not preferable and proper for the elastic evaluation. As will be described later, the value of the distance index is also used as one of values representing elastic evaluation values as reliable indexes of the ROI that is a measurement region.

Figure 7:
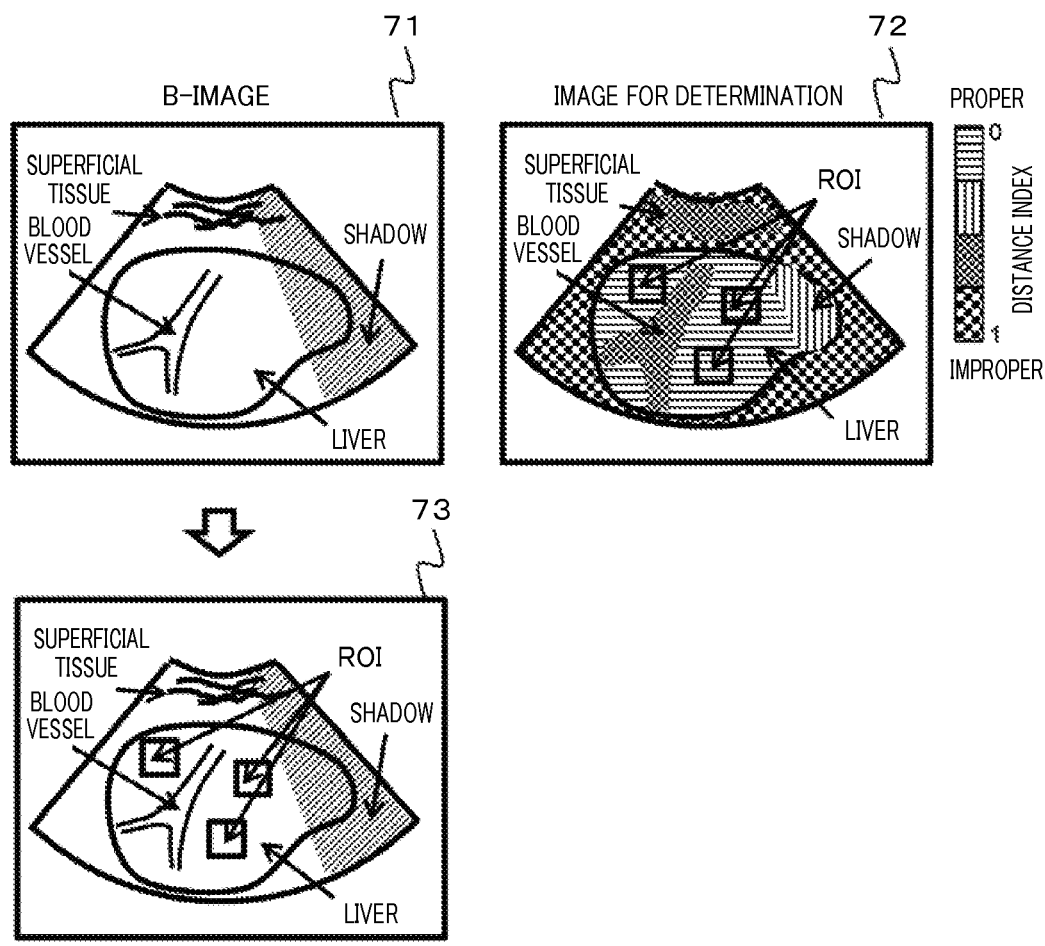
FIG. 7 is a diagram for showing an example of setting ROIs according to the first embodiment.

FIG. 7 shows an example of a B-image 71 for a liver, an image for determination 72, and an ROI setting image 73 that is a determination result. The image for determination 72 is displayed using a color map colored in accordance with the values of the distance indexes, and a color scale in accordance with the values of the distance indexes is displayed on the image for determination 72. For the convenience of illustration, FIG. 7 is shown in black and white. However, as compared to blood vessels, a low-brightness shadow region, and a high-brightness superficial region that can be confirmed on the B-image 71, the image for determination 72 is colored to indicate that the regions are improper for the measurement, as shown in the drawing. The ROIs proper for the measurement of the shear waves for the elastic evaluation are automatically set in accordance with the values of the calculated distance indexes as shown in the ROI setting image 73. It is obvious that an operator as a user may manually set the ROIs by reference to the values and colors of the image for determination 72 displayed on the display or the like.

When the determination of the ROIs that are measurement regions where the shear waves are measured for the elastic evaluation is completed, the burst waves that are the second ultrasonic waves to generate the shear waves and the track pulses that are the third ultrasonic waves to measure displacement are irradiated in the ROIs. The position of the irradiation of the burst waves that are the second ultrasonic waves is determined using the image for determination 72 used in the detection of the ROIs. Specifically, the image for determination 72 is displayed using a color map colored in accordance with the values of the distance indexes, and thus the position of the irradiation of the burst waves that are the second ultrasonic waves is determined on the basis of the distance indexes.

Figure 8:
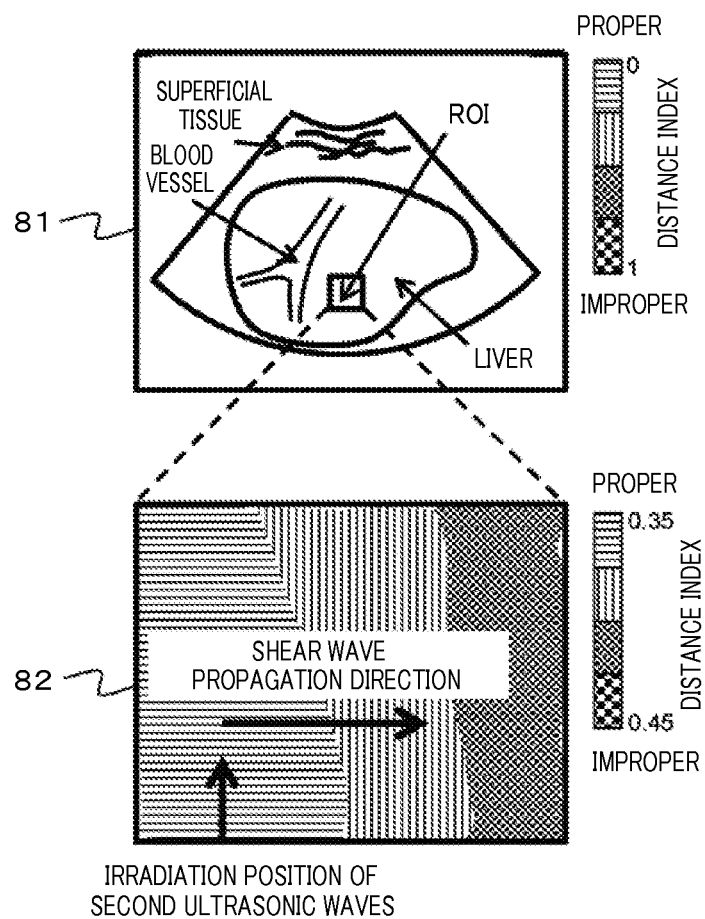
FIG. 8 is a diagram for showing determination of a position where second ultrasonic waves are irradiated according to the first embodiment.

A method of determining the position of the irradiation of the burst waves that are the second ultrasonic waves will be described using FIG. 8. FIG. 8 shows an image for determination 81 corresponding to the image for determination 71, and an in-ROI image for determination 82 enlarged by narrowing the display range of the distance index in the ROI extracted on the basis of the image for determination 81. The colors in the ROI that are difficult to be visually determined in the image for determination 81 can be definitely and visually confirmed in the enlarged in-ROI image for determination 82.

The burst waves to generate the shear waves need to be irradiated on a region as homogeneous as possible. Otherwise, the wavefront disorder occurs at the time of generation of the shear waves, and the affect is increased together with propagation. Further, the shear waves are attenuated dependently on frequencies. Specifically, the affects of diffraction and refraction caused by a tissue structure and a structural object are increased in the upstream containing high frequency components. Thus, for the measurement of the shear wave velocity in which the affect of the wavefront disorder is lessened, the burst waves are desirably irradiated on a region with a small distance index. Accordingly, the position of the irradiation of the burst waves that are the second ultrasonic waves in the embodiment is preferably determined on the basis of the distance index calculated by the ROI detection unit 21. The determination can be automatically made using the value (0 to 1) of the distance index. Further, an operator as a user can manually set the position of the irradiation of the burst waves using the in-ROI image for determination 82 that is displayed on the display and is illustrated and enlarged in FIG. 8.

The calculation of the shear wave velocity and the elastic evaluation on the basis of the shear wave velocity are performed in each ROI determined by the ROI detection unit 21. Specifically, the ROI that is a measurement region can be automatically set by determination using an index that is calculated on the basis of the brightness distribution of the image data and that objectively indicates a region proper for the elastic evaluation in the ultrasonic diagnostic apparatus in the embodiment. Therefore, the elastic evaluation with a high degree of reliability can be realized. In addition, improvement of operability of setting the ROI can be advantageously expected.

Figure 9:
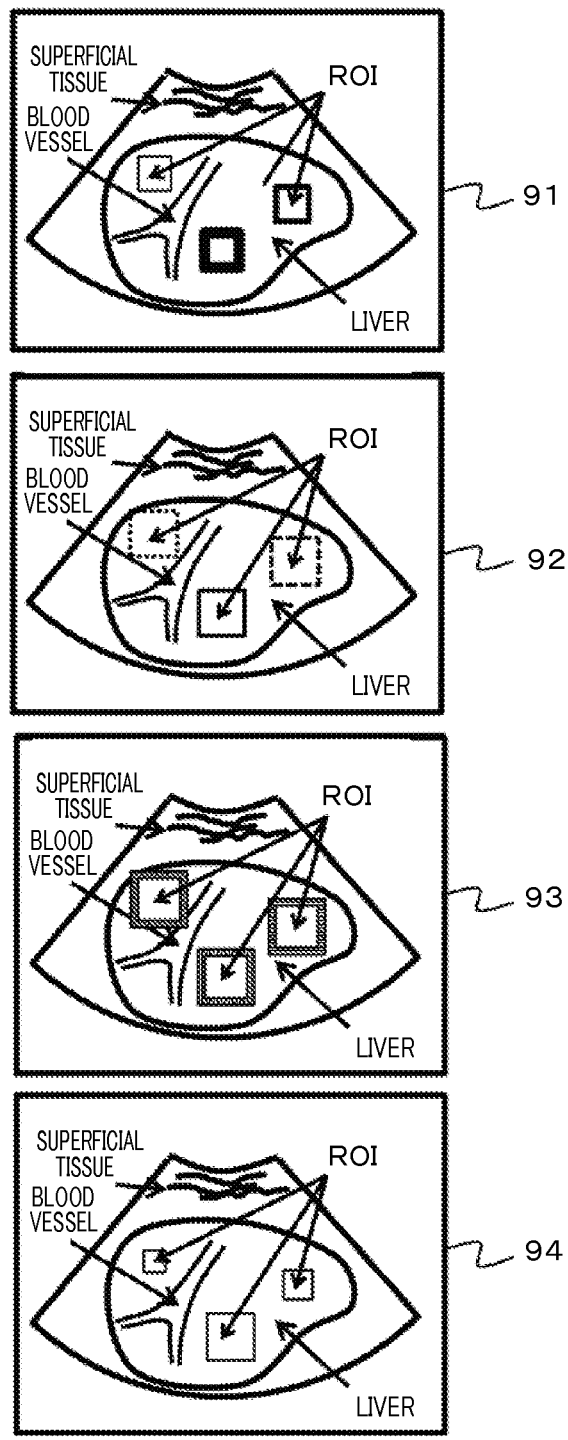
FIG. 9 is a diagram for showing an example of display configurations of setting the ROIs according to the first embodiment.

FIG. 9 shows an example of display configurations each showing a relative difference of the value of the distance index of each ROI on the display unit on the assumption that plural ROIs are set in the ultrasonic diagnostic apparatus of the embodiment. The relative differences of the distance indexes are shown using the thicknesses of frame lines showing the ROIs in a first display configuration 91 on the display of the drawing, the line types of the frame lines showing the ROIs in a second display configuration 92, the colors of the frame lines showing the ROIs in a third display configuration 93, and the sizes of the frames showing the ROIs in a fourth display configuration 94. Specifically, the distance indexes are displayed in visually-determinable configurations such as the sizes of the frame lines, the line types of the frame lines, the colors of the frame lines, and the sizes of the frames of the ROIs that are measurement regions displayed on the display unit 20. Such visual distinction can be easily used as diagnostic information by being reflected on the result of the elastic evaluation.

Next, FIG. 10 shows an example of a display configuration that displays elastic evaluation values that are reliability indexes of the result of the elastic evaluation on the display unit using colors in the ultrasonic diagnostic apparatus of the embodiment. For the convenience of illustration, FIG. 10 is shown in black and white. In the drawing, the values of the distance indexes calculated in respective measurement regions ROI1, ROI2, PORI3, and ROI4 are replaced by colors, and are displayed on a graph 101 representing the result of the elastic evaluation as the elastic evaluation values, namely, the reliability indexes. Further, a color scale of the degrees of reliability as the reliability indexes of the result is simultaneously displayed on the graph 101. The colors are set depending on the degrees of reliability in the color scale of the degrees of reliability in accordance with the values of the distance indexes. The signal processing unit 23 displays the elastic evaluation values that are the reliability indexes of the result of the elastic evaluation on the display unit 20. Accordingly, the degree of reliability of the result of the elastic evaluation in each measurement region ROI can be visually confirmed, and thus information used for diagnosis can be promptly and accurately extracted.

Further, the average value and the dispersion of the elastic evaluation values are presented as elastic evaluation values of "all ROIs" while limiting to the ROI that is determined as a high degree of reliability, so that the unevenness of elasticity of the entire tissue can be evaluated. In general, the dispersion of the measurement result represents accuracy. However, the dispersion of the elastic evaluation values displayed as "all ROIs" after calculating the elastic evaluation values using plural ROIs that are set in spatially-different positions on the basis of the ROI where the reliability is preliminarily evaluated represents the unevenness of elasticity in the same tissue rather than the accuracy. Thus, the dispersion can be used as diagnostic information of, for example, distribution of the progression rates and the sites of onset of disease.

According to the above-described configuration of the first embodiment, it is possible to provide an ultrasonic diagnostic apparatus with improved operability by which a highly-reliable and high-accuracy elastic evaluation can be performed using a method of automatically determining and setting an ROI as a measurement region proper for the elastic evaluation. It should be noted that the above-described configuration of the ultrasonic diagnostic apparatus is only an example, and includes various modified examples. For example, it is obvious that a signal processing unit using the RF data having the configurations of FIG. 1 and FIG. 2 and the image data stored in the cine memory can be used.

Second Embodiment

The second embodiment is an embodiment related to another method of calculating the shear wave velocity, and the like in the ROI that is a measurement region determined in the first embodiment. Specifically, the second embodiment is an embodiment of an ultrasonic diagnostic apparatus and an elastic evaluation method. The ultrasonic diagnostic apparatus includes a transmission/reception unit that transmits and receives first, second, and third ultrasonic waves to/from an inspection target through a probe that transmits and receives ultrasonic waves and a processing unit that processes received data obtained from the inspection target. The processing unit determines a measurement region on the basis of image information formed using the received data obtained by transmitting and receiving the first ultrasonic waves, transmits the second ultrasonic waves to the determined measurement region to generate shear waves, measures the wavefront characteristic amount of the shear waves at a first measurement point and a second measurement point using the received data obtained by transmitting and receiving the third ultrasonic waves to/from the measurement region, calculates a frequency distribution of peak-to-times(PT) of the shear waves at the first measurement point and the second measurement point, and calculates a shear wave velocity and an elastic evaluation value of the measurement region through a correlation operation of the frequency distribution. A frequency distribution can be represented by a histogram, a frequency table, and so on.

The constitutional elements themselves of the apparatus according to the second embodiment are the same as those of FIG. 1 and FIG. 2 provided in the first embodiment. Further, the processing content up to irradiating the second ultrasonic waves and the third ultrasonic waves onto the set ROI and measuring the PT of the wavefront of the shear waves at the measurement position that is preliminarily set in the propagation direction of the shear waves is the same as that in the first embodiment. Thus, the detailed explanation will be omitted.

Figure 12:
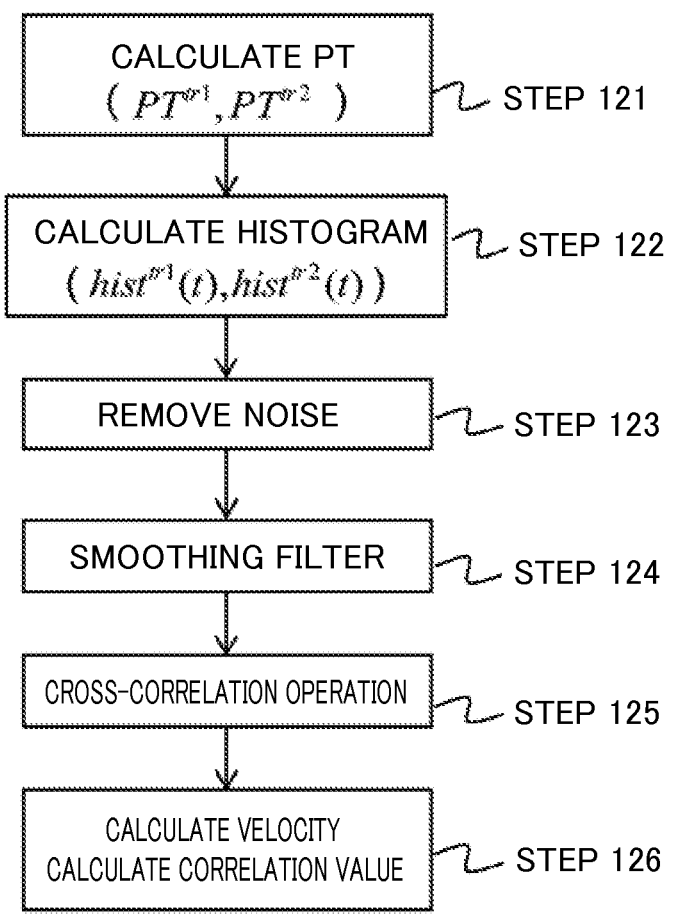
FIG. 12 is a diagram for showing a flowchart related to calculation of a velocity according to a second embodiment.

FIG. 12 shows a flowchart of processes leading to calculation of a shear wave velocity and an index indicating reliability using PT (Peak to time) calculated at each of plural measurement positions that are preliminarily set in the ultrasonic diagnostic apparatus of the second embodiment. The description of the embodiment assumes two measurement points, in total, of a first measurement point and a second measurement point from the upstream side of the propagation of ultrasonic waves along the propagation direction of shear waves. The PT measured at each measurement point is referred to as $PT^{tr1}$ or $PT^{tr2}$.

FIG. 13 shows an example of the results of measurement of displacement at the first measurement point and the second measurement point as a wavefront 131 at the first measurement point and a wavefront 132 at the second measurement point. The shear waves generated from the first ultrasonic waves are expanded in a certain range in the depth direction. The results obtained by measuring the propagation of the wavefronts by measurement of displacement can be obtained as shown in FIG. 13 in which the vertical axis represents a depth and the horizontal axis represents time. As described in the first embodiment, the PT of the wavefront is calculated using the wavefront characteristic amount such as a maximum value, a minimum value, and an intermediate value between the maximum value and the minimum value on the basis of time changes of displacement that are results of measurement of displacement.

In the embodiment, the explanation will be continued using a method of using the minimum value as the wavefront characteristic amount. In Step 122, the PT is first calculated at each point in the depth direction, and histograms $hist^{tr1}(t)$ and $hist^{tr2}(t)$ corresponding to the respective measurement points are calculated. The intervals between bins of a histogram 133 in FIG. 13 are adjusted in accordance with time intervals of measurement of displacement. In the embodiment, a histogram of the PT is calculated as an example of information representing a frequency distribution of the PT. Further, another feature value to show the wave distribution is available to calculate the frequency distribution.

Thereafter, noise is removed in Step 123. The removal method is performed according to a method that is generally used in the field of signal processing. For example, an outlier is removed with a significance level of 0.3% or a significance level of 5%. Thereafter, a smoothing filter is applied on the assumption that the histogram 133 is a polynomial function (Step 124). The type of smoothing filter is not particularly limited. However, it is necessary to determine the size in consideration of the wavelength of the shear waves. Basically, the size is set in a range not exceeding one fourth of the wavelength. FIG. 13 shows the histogram 133 calculated at the respective measurement points and a graph 134 of the results obtained by applying the smoothing filter. In this case, the results obtained by using a Gaussian filter are shown as an example.

In Step 125, a cross-correlation operation is performed using the histogram in which the smoothing filter is applied (Equation 6). The horizontal axis of the histogram represents a time axis, and identification of positions that are highly correlated with each other means calculation of the propagation time of the shear waves between the measurement points. Thus, the velocity of the shear waves is calculated using the result of the correlation operation and the distances between the measurement points. At the same time, a correlation value indicating the consistency of the histogram is calculated (Step 126).

The histogram of the respective measurement points represents the wavefront shapes at the positions. For example, in the case where the wavefront is largely disordered with the propagation, the shape of each histogram is largely changed. Thus, the calculated correlation value becomes small. Namely, the correlation value calculated using the cross-correlation operation between the histograms can be obtained by directly evaluating the reliability of the result of measurement of the velocity in the viewpoint of the wavefront disorder. Accordingly, in the ultrasonic diagnostic apparatus of the embodiment, the signal processing unit 23 displays the correlation value calculated using the correlation operation of the histogram on the display unit 20 as the elastic evaluation value of the reliability index of the shear wave velocity, as will be described later.

Figures 14, 15:
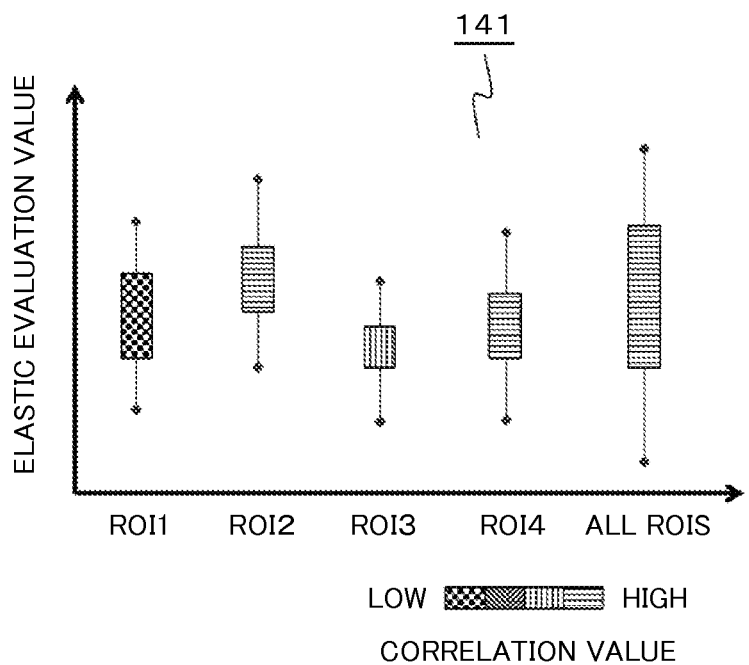
FIG. 14 is a diagram for showing an example of a display configuration of elastic evaluation results according to the second embodiment.
FIG. 15 is a diagram for showing equations related to processing methods according to the second embodiment.

FIG. 14 shows an example of a display configuration in the case where the correlation values are used as the elastic evaluation values, namely, the reliability indexes at the time of the elastic evaluation by the ultrasonic diagnostic apparatus of the second embodiment. As similar to FIG. 10, the values of the correlation values are expressed using different colors, and are reflected on the measurement results at the ROI1, ROI2, ROI3, and ROI4. According to the display configuration, an operator can visually determine a highly-reliable elastic evaluation value to be used as accurate diagnostic information.

Further, as similar to the case of FIG. 10, the value indexes indicating statistical interpretation such as the average value, the dispersion, and the standard deviation of the elastic evaluation values of the all ROIs are displayed together while limiting to the ROI where a highly-reliable elastic evaluation value can be obtained, so that new diagnostic information can be offered to an operator. Specifically, in the ultrasonic diagnostic apparatus of the embodiment, the signal processing unit 23 displays the dispersion or the standard deviation of the elastic evaluation values calculated in the ROIs that are plural measurement regions on the display unit 20 as an index, namely, "all ROIs" to determine unevenness of elasticity of the measurement target.

In general, the standard deviation of the measurement results represents affects of statistical errors and systematic errors. However, the value indexes in the all ROIs are calculated on the basis of the result in which the reliability of the measurement itself has been already evaluated, and represent the difference between the elastic evaluation values in the same tissue rather than the measurement errors. Specifically, the statistical value indexes of the elastic evaluation values in the all ROIs shown in FIG. 14 are presented as diagnostic information representing unevenness of the progression rates and the sites of onset of disease The effect of the embodiment can be enhanced by being combined with the ROI detection method described in the first embodiment in detail in which an index indicating a region proper for the elastic evaluation is calculated on the basis of the brightness distribution, and the measurement region is detected on the basis of the calculated index. The elastic evaluation with a high degree of accuracy is realized by the results of all processes in which the shear waves are allowed to be generated at proper regions, the shear wave velocity is detected at a high degree of accuracy, and the adequacy of the result is determined. Specifically, the ultrasonic diagnostic apparatus having the highly-reliable tissue elastic evaluation unit can be realized by using the ROI detection method using the index indicating a region proper for the elastic evaluation on the basis of the brightness information and the elastic evaluation method in which velocity detection by the cross-correlation operation on the basis of the histogram and calculation of the elastic evaluation value as the reliability index are performed.

Various embodiments of the present invention have been described above. However, the present invention is not limited to the above-described embodiments, but includes various modified examples. For example, the above-described embodiments have been described in detail for a better understanding of the present invention, and are not necessarily limited to those having the all configurations described above. Further, a part of the configuration in one embodiment can be replaced by a configuration of another embodiment, and the configuration in one embodiment can be added to another embodiment. For example, a signal processing unit having the configurations of FIG. 1 and FIG. 2 can be used. In addition, a part of the configuration in each embodiment can be added to or replaced by another, or deleted.

Further, the above-described configurations, functions, processing units, and the like have been described mainly using examples of creating programs realizing a part or all thereof. However, it is obvious that, for example, the scan converter, and the like may be realized using hardware by designing a part or all thereof using, for example, integrated circuits.

What is claimed:

1. An ultrasonic diagnostic apparatus comprising:
    a transmission/reception unit that transmits and receives first, second, and third ultrasonic waves to/from an inspection target through a probe that transmits and receives ultrasonic waves; and
    a processing unit that processes received data obtained from the inspection target,
    wherein the processing unit calculates an index indicating a region proper for an elastic evaluation based on brightness distribution of the inspection target calculated using image information formed using the received data obtained by transmitting and receiving the first ultrasonic waves, and determines a measurement region based on the index, transmits the second ultrasonic waves to the determined measurement region to generate shear waves, calculates a shear wave velocity using the received data obtained by transmitting and receiving the third ultrasonic waves to/from the measurement region, and outputs the shear wave velocity and an elastic evaluation value of the measurement region.

2. The ultrasonic diagnostic apparatus according to claim 1, wherein the processing unit includes:
an Region of Interest (ROI) detection unit that calculates the index based on the brightness distribution, and detects the measurement region based on the calculated index, and
an elastic evaluation unit that performs the elastic evaluation of the measurement region using the shear wave velocity measured at the measurement region.

3. The ultrasonic diagnostic apparatus according to claim 1, wherein the processing unit calculates the index based on a statistical value of brightness in a certain range of the inspection target, and uses, as the statistical value, the average value of brightness after an adjustment process by an s-shaped function.

4. The ultrasonic diagnostic apparatus according to claim 1, wherein a display unit is further provided, and the processing unit displays the value of the index on the display unit as a color map of the inspection target.

5. The ultrasonic diagnostic apparatus according to claim 1, wherein a display unit is further provided, and the processing unit displays the value of the index using the size of a frame line of the measurement region displayed on the display unit, the type of line, a color, or the size of a frame of the measurement region.

6. The ultrasonic diagnostic apparatus according to claim 1, wherein a display unit is further provided, and the processing unit calculates the elastic evaluation value of the measurement region based on the index, and displays the elastic evaluation value of the measurement region on the display unit.

7. The ultrasonic diagnostic apparatus according to claim 6, wherein the processing unit displays dispersion or standard deviation of the elastic evaluation values calculated at the plural measurement regions on the display unit as indexes to determine unevenness of elasticity of the measurement target.

8. The ultrasonic diagnostic apparatus according to claim 1, wherein the processing unit measures the wavefront characteristic amount of the shear waves at a first measurement point and a second measurement point using the received data obtained by transmitting and receiving the third ultrasonic waves to/from the measurement region, calculates a frequency distribution of peak to-times of the shear waves at the first measurement point and the second measurement point, and calculates the shear wave velocity and the elastic evaluation value of the measurement region through a correlation operation of the frequency distribution.

9. The ultrasonic diagnostic apparatus according to claim 8, wherein a display unit is further provided, and the processing unit displays a correlation value calculated through the correlation operation of the frequency distribution on the display unit as the elastic evaluation value of the measurement region.

10. The ultrasonic diagnostic apparatus according to claim 9, wherein the processing unit displays dispersion or standard deviation of the elastic evaluation values calculated at the plural measurement regions on the display unit as indexes to determine unevenness of elasticity of the measurement target.

11. The ultrasonic diagnostic apparatus according to claim 8, wherein the processing unit calculates a histogram of peak-to-times of the shear waves as information representing a frequency distribution of peak to-times of the shear waves.

12. An elastic evaluation method comprising the steps of:
transmitting and receiving first ultrasonic waves to/from an inspection target through a probe that transmits and receives ultrasonic waves;
generating brightness distribution of an inspection target based on received data obtained from the inspection target;
calculating an index indicating a region proper for an elastic evaluation based on brightness distribution of the inspection target;
determining a measurement region based on the calculated index;
transmitting second ultrasonic waves to the determined measurement region to generate shear waves;
calculating a shear wave velocity using the received data obtained by transmitting and receiving third ultrasonic waves to/from the measurement region; and
outputting the shear wave velocity and an elastic evaluation value of the measurement region.

13. The elastic evaluation method according to claim 12, further comprising the steps of:
measuring the wavefront characteristic amount of the shear waves at a first measurement point and a second measurement point using the received data obtained by transmitting and receiving the third ultrasonic waves to/from the measurement region;
calculating a frequency distribution of peak-to-times of the shear waves at the first measurement point and the second measurement point; and
calculating the shear wave velocity and the elastic evaluation value of the measurement region through a correlation operation of the frequency distribution.

14. The elastic evaluation method according to claim 13, further comprising the step of:
using dispersion or standard deviation of the elastic evaluation values calculated at the plural measurement regions as indexes to determine unevenness of elasticity of the measurement target.

* * * * *